United States Patent
Akin et al.

(10) Patent No.: US 10,603,802 B2
(45) Date of Patent: Mar. 31, 2020

(54) END REGION INSPECTION MODULE AND METHOD FOR IN SITU GAP INSPECTION ROBOT SYSTEM

(71) Applicant: General Electric Company, Schenectady, NY (US)

(72) Inventors: Selim Akin, Istanbul (TR); Thomas James Batzinger, Burnt Hills, NY (US); Airton Rosa da Silva, Jr., Schenectady, NY (US); Selami Haydar Icli, Zurich (CH); Christopher Paul Markman, Canton, GA (US); Paulo Cesar Debenest, Tokyo (JP); Michele Guarnieri, Tokyo (JP); Giorgio Valsecchi, Tokyo (JP); Shigeo Hirose, Tokyo (JP)

(73) Assignee: General Electric Company, Schenectady, NY (US)

( * ) Notice: Subject to any disclaimer, the term of this patent is extended or adjusted under 35 U.S.C. 154(b) by 335 days.

(21) Appl. No.: 15/652,771

(22) Filed: Jul. 18, 2017

(65) Prior Publication Data
US 2019/0022876 A1 Jan. 24, 2019

(51) Int. Cl.
*B25J 5/00* (2006.01)
*B62D 57/00* (2006.01)
(Continued)

(52) U.S. Cl.
CPC .............. *B25J 19/023* (2013.01); *B25J 5/00* (2013.01); *B62D 57/02* (2013.01); *G01N 21/954* (2013.01); *G01R 31/34* (2013.01); *H04N 5/2253* (2013.01); *H04N 5/2256* (2013.01); *H04N 5/2257* (2013.01); *H04N 5/23293* (2013.01);
(Continued)

(58) Field of Classification Search
None
See application file for complete search history.

(56) References Cited

U.S. PATENT DOCUMENTS

| 4,677,865 A | 7/1987 | Lehmann |
| 4,683,973 A | 8/1987 | Honjo et al. |

(Continued)

FOREIGN PATENT DOCUMENTS

| CH | 669127 A5 | 2/1989 |
| EP | 0171633 A1 | 2/1986 |

(Continued)

OTHER PUBLICATIONS

U.S. Appl. No. 15/652,859, Notice of Allowance dated May 15, 2019, 10 pgs.

(Continued)

*Primary Examiner* — Natalie Huls
*Assistant Examiner* — Jermaine L Jenkins
(74) *Attorney, Agent, or Firm* — Theodoros Stamatiadis; Hoffman Warnick LLC

(57) ABSTRACT

This disclosure provides systems and methods for in situ gap inspection in a machine, such as a generator, an electric motor, or a turbomachine, with an end region. A robotic crawler is configured to navigate an annular gap of the machine. A visual inspection module is connected to the robotic crawler and includes an extension member for extending a camera into the end region to collect visual inspection data.

18 Claims, 8 Drawing Sheets

(51) Int. Cl.

| | | |
|---|---|---|
| *G01N 21/954* | (2006.01) | |
| *B25J 19/02* | (2006.01) | |
| *H04N 5/225* | (2006.01) | |
| *H04N 5/232* | (2006.01) | |
| *B62D 57/02* | (2006.01) | |
| *G01R 31/34* | (2020.01) | |
| *B62D 57/024* | (2006.01) | |

(52) U.S. Cl.
CPC ....... *H04N 5/23296* (2013.01); *B62D 57/024* (2013.01); *H04N 5/2252* (2013.01); *H04N 2005/2255* (2013.01); *Y10S 901/44* (2013.01)

(56) References Cited

U.S. PATENT DOCUMENTS

| | | | |
|---|---|---|---|
| 4,889,000 | A | 12/1989 | Jaafar et al. |
| 4,970,890 | A | 11/1990 | Jaafar et al. |
| 5,172,639 | A | 12/1992 | Wiesman et al. |
| 5,650,579 | A | 7/1997 | Hatley et al. |
| 5,788,002 | A | 8/1998 | Richter |
| 5,947,051 | A | 9/1999 | Geiger |
| 5,969,531 | A | 10/1999 | Murakami et al. |
| 6,100,711 | A | 8/2000 | Hatley |
| 6,404,189 | B2 | 6/2002 | Kwun et al. |
| 6,814,169 | B2 | 11/2004 | Moore et al. |
| 6,876,222 | B2 | 4/2005 | Fischer et al. |
| 6,889,783 | B1 | 5/2005 | Moore et al. |
| 6,917,176 | B2 | 7/2005 | Schempf et al. |
| 6,959,603 | B2 | 11/2005 | Knight et al. |
| 7,188,568 | B2 | 3/2007 | Stout |
| 7,201,055 | B1 | 4/2007 | Bagley et al. |
| 7,218,993 | B2 | 5/2007 | Yasukawa et al. |
| 7,331,436 | B1 | 2/2008 | Pack et al. |
| 7,520,189 | B2 | 4/2009 | Abbasi et al. |
| 7,600,593 | B2 | 10/2009 | Filippov et al. |
| 7,617,732 | B2 * | 11/2009 | Bui ...................... G01N 29/043 73/618 |
| 7,624,827 | B2 | 12/2009 | Moser et al. |
| 7,654,348 | B2 | 2/2010 | Ohm et al. |
| 7,681,452 | B2 | 3/2010 | Bagley et al. |
| 7,743,675 | B2 | 6/2010 | Moore |
| 7,866,421 | B2 | 1/2011 | Moore et al. |
| 7,891,445 | B1 | 2/2011 | McKinley et al. |
| 8,028,775 | B2 | 10/2011 | Orenbuch |
| 8,220,345 | B2 | 7/2012 | Moser et al. |
| 8,477,891 | B2 | 7/2013 | Wallace et al. |
| 8,568,299 | B2 | 10/2013 | Eno et al. |
| 8,571,711 | B2 | 10/2013 | Jacobsen et al. |
| 8,619,134 | B2 * | 12/2013 | Christ ...................... G01N 21/952 348/84 |
| 8,839,684 | B2 | 9/2014 | Banowetz et al. |
| 9,031,698 | B2 | 5/2015 | Smith |
| 9,056,746 | B2 | 6/2015 | Mehrandezh et al. |
| 9,217,852 | B2 | 12/2015 | Baleine |
| D748,053 | S | 1/2016 | Herrlich et al. |
| D756,922 | S | 5/2016 | Herrlich et al. |
| 9,398,198 | B2 | 7/2016 | Choi et al. |
| 9,409,292 | B2 * | 8/2016 | Smith ...................... B25J 9/065 |
| 9,683,460 | B2 | 6/2017 | Moore et al. |
| 9,708,934 | B2 | 7/2017 | Moore et al. |
| 9,759,667 | B2 | 9/2017 | Miasnikov et al. |
| 9,808,140 | B2 | 11/2017 | Belson et al. |
| 9,989,970 | B1 * | 6/2018 | Morey ...................... B62D 57/022 |
| 10,488,350 | B2 * | 11/2019 | Lakhani ............... H04N 5/2256 |
| 2002/0104693 | A1 | 8/2002 | Moore et al. |
| 2002/0190682 | A1 | 12/2002 | Schempf et al. |
| 2004/0020002 | A1 * | 2/2004 | Moore ............... B62D 57/024 15/340.1 |
| 2004/0099175 | A1 | 5/2004 | Perrot et al. |
| 2004/0173116 | A1 | 9/2004 | Ghorbel et al. |
| 2005/0104600 | A1 | 5/2005 | Cotton |
| 2008/0087112 | A1 | 4/2008 | Bagley et al. |
| 2008/0098832 | A1 | 5/2008 | Abbasi et al. |
| 2008/0121041 | A1 | 5/2008 | Smith et al. |
| 2008/0179115 | A1 | 7/2008 | Ohm et al. |
| 2008/0308324 | A1 | 12/2008 | Moser et al. |
| 2009/0120215 | A1 | 5/2009 | Jacobson et al. |
| 2009/0146680 | A1 | 6/2009 | Moser et al. |
| 2009/0171151 | A1 | 7/2009 | Choset et al. |
| 2011/0040427 | A1 | 2/2011 | Ben-Tzvi |
| 2012/0069172 | A1 * | 3/2012 | Hudritsch ............ G01N 21/954 348/84 |
| 2012/0205168 | A1 * | 8/2012 | Flynn ...................... B25J 5/005 180/9.1 |
| 2013/0231779 | A1 | 9/2013 | Purkayastha et al. |
| 2014/0022374 | A1 | 1/2014 | Brignac et al. |
| 2014/0067185 | A1 | 3/2014 | Tralshawala et al. |
| 2014/0216836 | A1 | 8/2014 | Davies et al. |
| 2014/0345384 | A1 | 11/2014 | Nguyen |
| 2015/0233787 | A1 | 8/2015 | Eakins et al. |
| 2015/0251318 | A1 | 9/2015 | Lv |
| 2015/0323469 | A1 | 11/2015 | Clayton et al. |
| 2016/0075020 | A1 | 3/2016 | Szarski et al. |
| 2016/0239080 | A1 | 8/2016 | Marcolina et al. |
| 2017/0362068 | A1 | 12/2017 | Cheng |
| 2018/0021945 | A1 | 1/2018 | Pettersen et al. |
| 2018/0313715 | A1 * | 11/2018 | Cichosz ............... B60B 19/003 |

FOREIGN PATENT DOCUMENTS

| | | |
|---|---|---|
| EP | 0390352 A2 | 10/1990 |
| EP | 1863153 A2 | 12/2007 |
| EP | 2345902 A1 | 7/2011 |
| EP | 2743447 A1 | 6/2014 |
| FR | 2355236 A1 | 1/1978 |
| JP | 2007256262 A | 10/2007 |
| WO | 9702452 | 1/1997 |
| WO | 2008076193 A2 | 6/2008 |
| WO | 2015095543 A1 | 6/2015 |
| WO | 2016138529 A1 | 9/2016 |
| WO | 2016141769 A1 | 9/2016 |

OTHER PUBLICATIONS

U.S. Appl. No. 15/652,805, Office Action dated Jun. 27, 2019, 13 pgs.
U.S. Appl. No. 15/652,680, Notice of Allowance dated Jul. 17, 2019, 8 pgs.
International Search Report and written opinion for corresponding PCT Application No. PCT/US2018/037900 dated Sep. 13, 2018, 14 pages.
U.S. Appl. No. 15/652,859, Office Action dated Feb. 19, 2019, 17 pages.
International Search Report and written opinion for corresponding PCT Application No. PCT/US2018/041726 dated Oct. 29, 2018, 16 pages.
U.S. Appl. No. 15/652,680, Office Action dated Mar. 18, 2019, 22 pages.
International Search Report and written opinion for corresponding PCT Application No. PCT/US2018/035329 dated Sep. 11, 2018, 18 pages.
International Search Report and written opinion for corresponding PCT Application No. PCT/US2018/038453 dated Oct. 25, 2018, 17 pages.
International Search Report and written opinion for corresponding PCT Application No. PCT/US2018/040982 dated Oct. 17, 2018, 15 pages.
U.S. Appl. No. 15/652,730, Notice of Allowance dated May 3, 2019, 9 pages.
International Search Report and Written Opinion for PCT Application No. PCT/DK96/00298 dated Oct. 17, 1996, 25 pages.
U.S. Appl. No. 15/652,805, Notice of Allowance dated Jan. 15, 2020, 19 pgs.

* cited by examiner

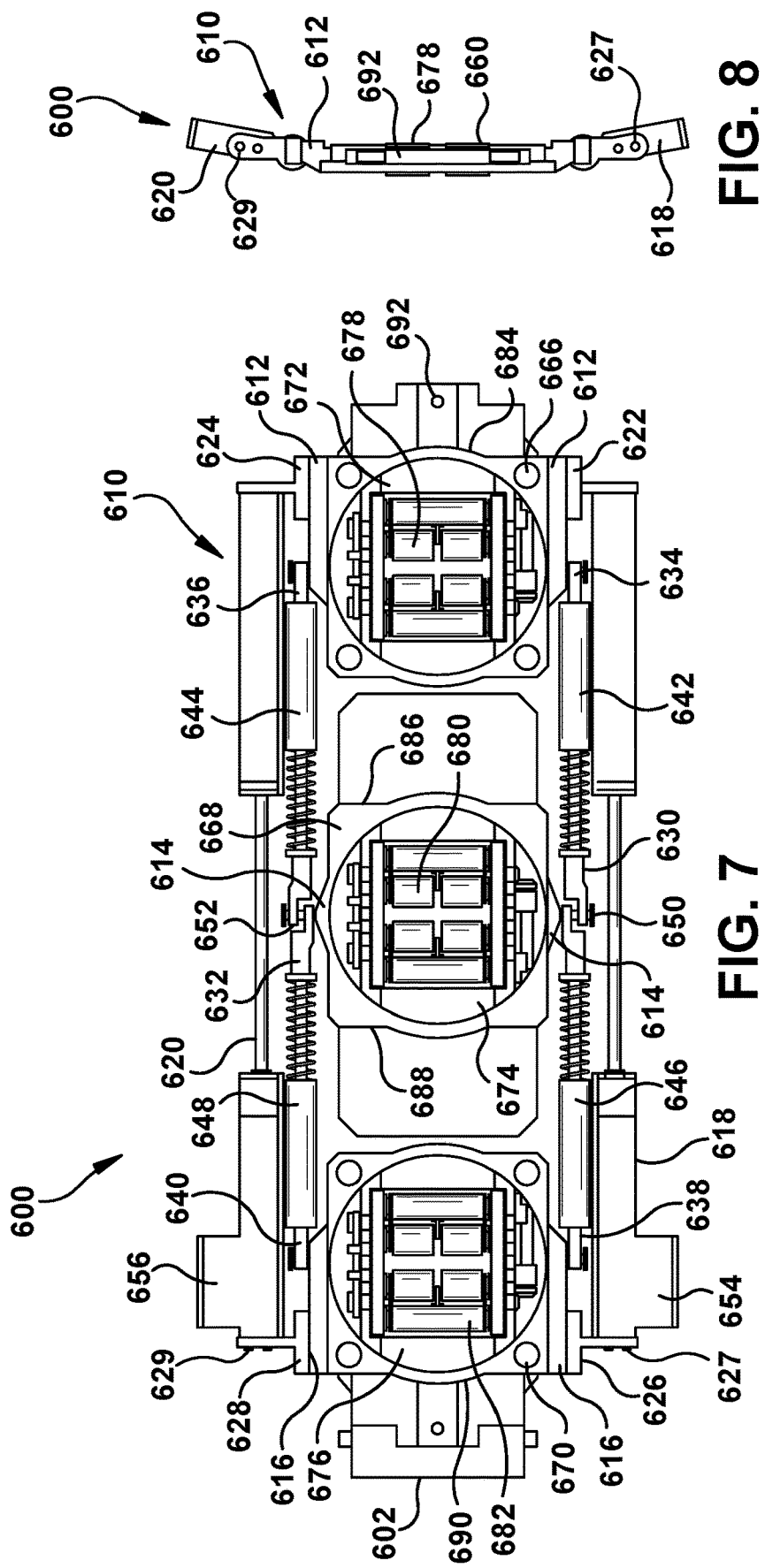

END REGION INSPECTION MODULE AND METHOD FOR IN SITU GAP INSPECTION ROBOT SYSTEM

BACKGROUND OF THE INVENTION

The disclosure relates to inspection of machinery and, more specifically, inspection using a robot inserted into an annular gap space, such as an air gap, in a generator, electric motor, or turbomachine, including turbo-generators.

The disclosure is related to concurrently filed U.S. patent application Ser. No. 15/652,730, entitled "MODULAR CRAWLER ROBOT FOR IN SITU GAP INSPECTION" filed Jul. 18, 2017, the entire contents of which are incorporated herein by reference. The disclosure is related to concurrently filed U.S. patent application Ser. No. 15/652,680, entitled "IN SITU GAP INSPECTION ROBOT SYSTEM AND METHOD" filed Jul. 18, 2017, the entire contents of which are incorporated herein by reference. The disclosure is related to concurrently filed U.S. patent application Ser. No. 15/652,859, entitled "OMNIDIRECTIONAL TRACTION MODULE FOR A ROBOT" filed Jul. 18, 2017, the entire contents of which are incorporated herein by reference. The disclosure is related to concurrently filed U.S. patent application Ser. No. 15/652,805, entitled "ACTUATED SENSOR MODULE AND METHOD FOR IN SITU GAP INSPECTION ROBOTS" filed Jul. 18, 2017, the entire contents of which are incorporated herein by reference.

A visual, mechanical, and/or electrical inspection and testing of a generator, electric motor, or turbomachine should be performed on a periodic basis. For example, generators may be inspected and tested periodically in the field for stator wedge tightness, visual surface anomalies, electromagnetic core imperfections, etc. Generator/stator inspection and testing procedures may require complete disassembly of the stator and removal of the generator rotor from the stator before any inspections or tests can be performed on the unit. The cost of disassembly and removal of the rotor, the time it takes for this process, and the dangers of rotor removal may impact the frequency of such inspections.

In situ inspection of generators has been performed employing poles, trolleys, scopes, and rotor turning techniques. These procedures may not accomplish the inspection task in a complete, timely, or safe manner.

Use of a robotic crawler capable of insertion through the air gap between the core iron and the retaining ring permits in situ inspection of the rotor and the stator core. The crawler may be inserted in a collapsed position into the gap and expanded by spring return pneumatic rams to the width of the air gap. The crawler may be remotely controlled by a technician and provides video cameras and other inspection tools to perform generator rotor and stator inspections within the air gap as the crawler is driven to selected locations. The crawler may be maneuvered by the technician within the air gap using video for both navigation and visual inspection.

BRIEF DESCRIPTION OF THE INVENTION

A first aspect of this disclosure provides a system for end region inspection using an in situ gap inspection robot. A robotic crawler configured to navigate within an annular gap of a machine. A visual inspection module is connected to the robotic crawler and includes an extension member and at least one camera. A visual display is in communication with the robotic crawler and configured to display visual inspection data from the at least one camera to a user.

A second aspect of the disclosure provides a method for end region inspection using an in situ gap inspection robot. A first end portion at a first end of a machine, the machine selected from a generator, an electric motor, or a turbomachine, is removed to expose an entrance gap into an annular gap of the machine. A robotic crawler is inserted through the entrance gap into the annular gap of the machine. The annular gap is traversed by the robotic crawler to a crawler position adjacent a second end portion of the machine at a second end opposite the first end. A visual inspection of the second end portion of the machine is performed using a visual inspection module connected to the robotic crawler and including an extension member and at least one camera.

A third aspect of the disclosure provides a visual inspection module for a robotic crawler used in in situ gap inspection. A crawler interface is configured for removable attachment to the robotic crawler. An extension member extends from the crawler interface and is configured to extend from the robotic crawler positioned in an annular gap of a machine. At least one camera is disposed at a distal end of the extension member and positionable to collect visual data from the end portion of the machine. At least one communication channel is configured to receive control signals to the visual inspection module and provide visual data to a visual display.

The illustrative aspects of the present disclosure are arranged to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which:

FIG. 7 shows a top view of the robotic crawler of FIG. 6 in its collapsed state.

FIG. 8 shows an end view of the robotic crawler of FIG. 6 in its collapsed state.

Figure 1:
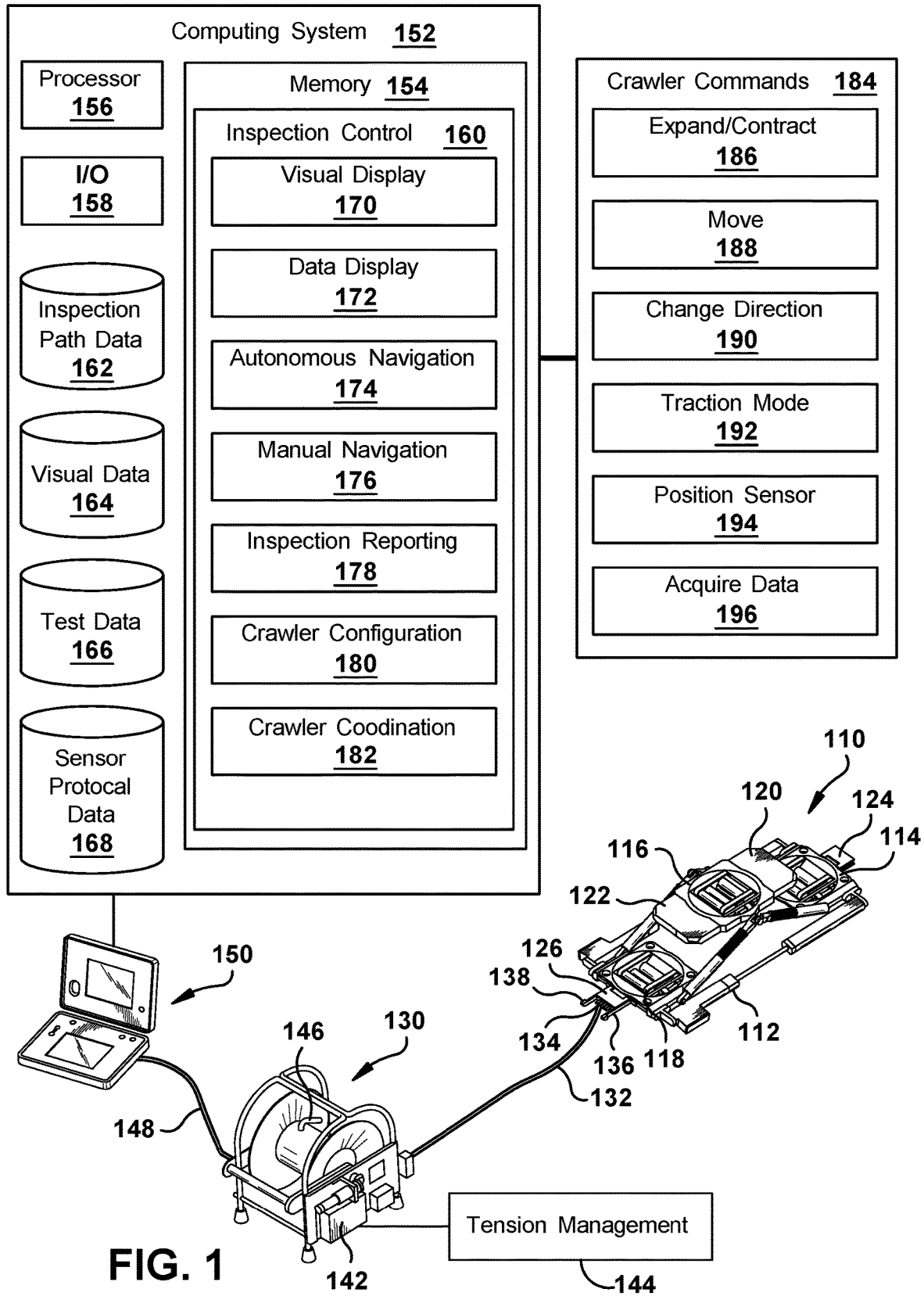
FIG. 1 shows a diagram of an example system for in situ gap inspection according to various embodiments of the disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be used and that changes may be made without departing from the scope of the present teachings. The following description is, therefore, merely illustrative.

Where an element or layer is referred to as being "on," "engaged to," "disengaged from," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Referring to FIG. 1, an example system 100 for in situ gap inspection is shown. System 100 may include a robotic crawler 110, a tether reel 130, and a control system 150. Robotic crawler 110 may be configured to be inserted through an entrance gap into an annular gap in a machine to conduct autonomous or semi-autonomous inspection of the machine. For example, robotic crawler 110 may be a collapsible robot that can operate in a collapsed or expanded state and may be inserted through a narrow entrance gap in its collapsed state and expand to a wider gap width such that it engages the opposed surfaces of the annular gap. Robotic crawler 110 is shown in its expanded state in FIG. 1. Once in the annular gap, robotic crawler 110 may navigate the annular gap and use one or more sensor modules to conduct various inspection tests during its movements or at various desired crawler positions in the annular gap. Robotic crawler 110 may be configured for multidirectional movement, including forward and reverse movement in the axial direction and bi-directional lateral movement in the circumferential direction. In some embodiments, robotic crawler 110 may be configured for omnidirectional movement that includes bi-directional movement in any orientation between the axial and circumferential directions, in addition to the axial and circumferential directions. For example, robotic crawler 110 may be configured to move in any direction in a 360 degree arc and freely change its direction of travel to any orientation in the 360 degree arc, including a plurality of directions between and angled from the axial and circumferential directions. In some embodiments, robotic crawler 110 may include a tether 132 connected to robotic crawler 110 and extending out of the machine during operation. For example, tether 132 may be a cable connected to robotic crawler 110 to enable retrieval of robotic crawler 110 in the event that robotic crawler 110 cannot navigate out of the annular gap under its own power. In some embodiments, tether 132 may provide a physical connection from robotic crawler 110 for a wired communication channel and/or a remote power source and/or pneumatic or hydraulic lines to support test systems or robotic operation. Tether reel 130 may be automated to adjust the tension and/or slack on tether 132 during operation of robotic crawler 110 within the annular gap, enabling robotic crawler 110 to navigate various navigation paths and perform inspection routines without a user manually managing the position of the tether. Control system 150 may be in communication with robotic crawler 110 to provide control signals to robotic crawler 110 and receive sensor, navigation, and/or other operational data from robotic crawler 110. In some embodiments, control system 150 may be electrically connected to tether 132 directly or through tether reel 130 and the electrical connection may include one or both of a power channel and a communication channel. Control system 150 may provide a user interface for a user to monitor, evaluate, supplement, and/or control robotic crawler 110 during an inspection deployment within the annular gap of the machine.

In some embodiments, robotic crawler 110 is a modular robot that may be reconfigured for different inspection tasks and enabling efficient maintenance, replacement, and/or upgrade of individual modules. Robotic crawler 110 may include a body frame, such as an expandable body 112, for receiving, positioning, and connecting various modules relative to one another. In some embodiments, expandable body 112 accommodates a plurality of traction modules 114, 116, 118. For example, robotic crawler 110 may include three traction modules 114, 116, 118, a forward traction module 114, a middle traction module 116, and a rear traction module 118, where forward traction module 114 and rear traction module 118 are configured to engage a first surface in the annular gap and the middle traction module 116 is configured to engage an opposed second surface in the annular gap. Traction modules 114, 116, 118 may be multidirectional traction module capable of moving robotic crawler 110 in multiple directions, including both axial and circumferential movement within the annular gap. Robotic crawler 110 may further include a plurality of sensor modules 120, 122, such as visual sensors for navigation and/or visual inspection. For example, sensor modules 120, 122 may be attached via sensor interfaces on the forward and rear sides of middle traction module 116 and may provide both forward and rear facing navigation cameras, as well as one or more upward facing cameras for inspecting the adjacent surface of the annular gap. Robotic crawler 110 may also include one or more tether connectors 124, 126 for detachably receiving tether 132, generally with a compatible end connector 134 and fasteners 136, 138.

In some embodiments, tether reel 130 is an automated tether reel that may receive, release, and spool tether 132 to adjust tension as needed during operation of robotic crawler 110. For example, tether reel 130 may include a servo motor 142 and tension management logic 144. For example, servo motor 142 operating in a torque/current control mode may detect changes in tension on tether 132 as it enters tether reel 130 and tension management logic 144 may provide an algorithm for maintaining an acceptable tension range using servo motor 142 to reel in or reel out tether 132 under closed loop control. In some embodiments, tether 132 may have a fixed connection 146 to tether reel 130 and a separate wire 148 may connect to control system 150. For example, wire 148 may provide communication and/or power channels without providing the mechanical characteristics desired for tethering robotic crawler 110. In some embodiments, tether reel 130 may provide an interface for receiving control signals for tether reel 130 from control system 150. For example, control system 150 may be able to adjust tension control or motor parameters and/or manually override operation of tether reel 130. In some embodiments, robotic crawler 110 may operate without a tether, carry its own power (e.g. batteries), and/or use wireless communication with control system 150.

In some embodiments, control system 150 may include a computing system 152. Computing system 152 may provide a plurality of programmatic controls and user interface for operating robotic crawler 110. In some embodiments, computing system 152 is a general purpose computing devices, such as a personal computer, work station, mobile device, or an embedded system in an industrial control system (using general purpose computing components and operating systems). In some embodiments, computing system 152 may be a specialized data processing system for the task of controlling operation of system 100. Computing system 152 may include at least one memory 154, processor 156, and input/output (I/O) interface 158 interconnected by a bus. Further, computing system 152 may include communication with external I/O device/resources and/or storage systems, including connected system, such as robotic crawler 110, tether reel 130, and network resources. In general, processor 156 executes computer program code, such as inspection control module 160, that is stored in memory 154 and/or a storage system. While executing computer program code, processor 156 can read and/or write data to/from memory 154, storage systems, and I/O devices (through I/O interface 158). The bus provides a communication link between each of the components within computing system 152. I/O devices may comprise any device that enables a user to interact with computing system 152 (e.g., keyboard, pointing device, display, etc.). Computing system 152 is only representative of various possible combinations of hardware and software. For example, the processor may comprise a single processing unit, or be distributed across one or more processing units in one or more locations, e.g., on a client and server. Similarly, memory and/or storage systems may reside at one or more physical locations. Memory and/or storage systems can comprise any combination of various types of non-transitory computer readable storage medium including magnetic media, optical media, random access memory (RAM), read only memory (ROM), etc. In some embodiments, computing system 152 is a laptop computer in communication with robotic crawler 110 via a wired (serial, USB, Ethernet, etc.) or wireless (802.11, Bluetooth, etc.) connection and running application software for system 100. In some embodiments, some or all of the functions of computing system 152 may be on board robotic crawler 110 using an integrated computing system, such as an on board control module, with or without wireless communication to one or more user interfaces and/or remote data storage.

In some embodiments, computing system 152 may include one or more application programs, data sources, and/or functional modules for controlling robotic crawler 110. For example, computing system 152 may include inspection control module 160 that operates in conjunction with data sources 162, 164, 166, 168 to provide control signals to and receive data from robotic crawler 110. Inspection control module 160 may provide a visual display module 170. For example, visual data collected by cameras on robotic crawler 110 may be displayed by visual display module 170, such as a graphical user interface for one or more video feeds. In some embodiments, visual data from robotic crawler 110 may be stored in visual data source 164 for use by visual display module 170 and/or selective, temporary, and/or archival storage of visual data for later use, including use by other users or systems. Data display module 172 may provide display, including visual display, of other test data, including processed visual data and resulting calculations or analysis. For example, data display module 172 may include a graphical user interface for test results from one or more test protocols using sensor and navigation data from robotic crawler 110. In some embodiments, test data from robotic crawler 110 may be stored in test data source 166 for use by data display module 172 and/or selective, temporary, and/or archival storage of test data for later use, including use by other users or systems. Data display module 172 may include a real-time display of test data as it is collected by robotic crawler 110 and/or one or more functions for viewing, aggregating, analyzing, visualizing, selecting, and/or reporting test data from test data source 166. Autonomous navigation module 174 may provide a protocol or series of commands for navigation of robotic crawler 110 within the annular gap of the machine. In some embodiments, autonomous navigation module 174 enables a user to select an inspection path from a plurality of inspection paths stored in inspection path data source 162. For example, inspection paths may be defined as physical paths robotic crawler 110 should follow within the annular gap to complete one or more inspection tasks in one or more locations within the annular gap. Inspection paths may be based on a physical schematic or parameters of one or more machines defining axial and circumferential distances. Inspection paths may also include parameters and locations related to specific features of interest for either navigation (e.g., surface features to be avoided) or for testing (e.g., locations or corresponding crawler positions for conducting specific tests). In some embodiments, inspection paths may be stored and defined in terms of a sequence of crawler commands. Autonomous navigation module 174 may enable autonomous navigation by robotic crawler 110 receiving and executing a sequence of crawler commands without user intervention once the autonomous operation is initiated. In some embodiments, autonomous navigation module 174 may have completely autonomous inspection routines that require no user intervention once initiated or may include a plurality of inspection subroutines, such as specific movement patterns, position changes, or test protocols, that are initiated in a desired sequence by a user, potentially based on navigational, visual, or test data feedback. Manual navigation module 176 may provide a user with the ability to pilot or otherwise control robotic crawler 110. In some embodiments, manual navigation module 176 may be provided for establishing an initial position for initiating automated control and/or allow a user to override automated control in response to problems, exceptions, or specific test protocols (such as an initial test result that requires further data gathering). In some embodiments, control system 150 may include one or more user I/O interfaces for manually controlling robotic crawler 110, such as joysticks and other tactile controls, for navigation, deploying sensors, and conducting various test protocols. Inspection module 178 may provide a plurality of routines for various inspection protocols using one or more sensor modules 120,122. In some embodiments, one or more sensor protocols are stored in sensor protocol data source 168 for use by inspection module 178. For example, a visual inspection protocol may include activating and capturing visual data from one or more sensor modules 120,122 on robotic crawler 110 along a defined navigation path to enable mapping of captured visual data to location information with the machine. In some embodiments, a plurality of cameras with varying facings and/or positionable cameras may be present in one or more sensor modules 120,122 and a visual inspection module may include selective activation and positioning of robotic crawler 110 and its various cameras. An inspection protocol executed by inspection module 178 may include a combination of navigational elements (navigation path, autonomous positioning, and/or manual positioning) and sensor protocols (position requirements, deployment, activation, timing/sampling, parameters, etc.). In some embodiments, inspection module 178 may define the storage of visual data and test data in visual data source 164 and test data source 166 and/or the display of visual data by visual display module 170 and test data by data display module 172. Crawler configuration module 180 may provide data regarding the configuration of modules and related capabilities and protocols for any given configuration of robotic crawler 110. In some embodiments, crawler configuration module 180 may map crawler configurations to machine specifications and sensor protocols to assist a user in matching inspection protocols with the resources available for a given test deployment. For example, a given configuration of sensor modules may define the test capabilities of robotic crawler 110 and recommend specific inspection protocols to utilize those sensor modules. In some embodiments, crawler configuration module 180 may include a library of sensor modules and related capabilities and support user reconfiguration of robotic crawler 110 for a desired inspection protocol. Crawler configuration module 180 may also define the set of crawler commands 184 that may be used to control robotic crawler 110. Crawler coordination module 182 may enable inspection control module 160 to control more than one robotic crawler 110 simultaneously. In some embodiments, crawler coordination module 182 may maintain a plurality of communication channels for control signals and data signals with a plurality of robotic crawlers. For example, crawler coordination module 182 may manage a plurality of instances of visual display module 170, data display module 172, autonomous navigation module 174, manual navigation module 176, inspection module 178, and crawler configuration module 180 for parallel management of the plurality of robotic crawlers. In some embodiments, crawler coordination module 182 may include interference protection for tracking the current crawler positions, navigation paths, and timing of various movements and sensor protocols to prevent collisions or other interference within the annular gap.

In some embodiments, visual display module 170, data display module 172, autonomous navigation module 174, manual navigation module 176, and inspection module 178 may include issuing one or more crawler commands 184 to robotic crawler 110 to complete some aspect of their function. Crawler commands 184 may then be translated into messages or control signals from control system 150 to robotic crawler 110. In some embodiments, crawler configuration module 180 may define the set of crawler commands available to the other modules based on the configuration of robotic crawler 110. An example set of crawler commands 184 are provided, but will be understood to be neither exclusive nor exhaustive of the possible crawler commands that could be used to control robotic crawler 110 and various configurations of traction modules, sensor modules, and body frame mechanics possible. Robotic crawler 110 may receive expand/contract commands 186 to expand or contract expandable body 112 between a collapsed state and one or more expanded states, such as a control signal to one or more motors that drive the body position. In some embodiments, expand or contract may be based on feedback from sensors within robotic crawler 110 when the traction modules are in a planar position (for collapsed state) or have contacted opposed surfaces in the annular gap (for expanded state). In other embodiments, expand or contract may be based on time (e.g., activate motor for x seconds of expansion or contraction) or distance (e.g., set crawler width to y inches). Robotic crawler 110 may receive move commands 188 to drive its traction modules forward or backwards (based on the present alignment of the traction modules in the case of multidirectional traction modules). Robotic crawler 110 may receive change direction commands 190 to reorient its traction modules and direction of travel. For example, change direction commands 190 may allow multidirectional traction modules to rotate 90 degrees and change from axial orientation and directions of travel to circumferential orientation and directions of travel. In some embodiments, change direction commands 190 may include orientation changes of greater or less than 90 degrees and include a feedback signal for confirming orientation or traction modules and communicating orientation back to control system 150. Robotic crawler 110 may receive traction mode commands 192 to drive changes in the configuration of the traction modules for different traction modes. For example, traction modules may include a flat mode for robot insertion and/or low profile and smooth surface travel and a clearance mode for providing clearance between the body of robotic crawler 110 and the surfaces it is moving along and/or traversing obstacles or uneven surfaces. Traction mode commands 192 may include control signals to change from flat mode to clearance mode or from clearance mode to flat mode. Robotic crawler 110 may receive position sensor commands 194 for sensor modules that include deployment and/or positioning features. For example, some sensor modules may include electromechanical features for extending, raising, lowering, rotating, or otherwise positioning one or more elements of the sensor module before, during, or after data collection. Position sensor commands 194 may include a control signal to activate a motor for extending or otherwise repositioning a sensor from robotic crawler 110 to position it for data collection or for moving a sensor (such as by rotation) independent of changing crawler position during data collection. Robotic crawler 110 may receive acquire data commands 196 for initiating data collection through a sensor module using whatever modality is present in that sensor module. Acquire data commands 196 may provide a start or stop signal for a continuous data collection mode, such as a video feed from the camera(s) of a visual sensor, or a specific test sequence for a more discrete sensor test, such as a mechanical wedge tightness test. It will be understood that some robotic crawlers and control systems may be able to communicate and manage multiple commands in parallel, as overlapping sequences, or as serial command series. Crawler coordination module 182 may enable control system 150 to issue commands to and acquire data from multiple robotic crawlers in parallel.

Figure 2:
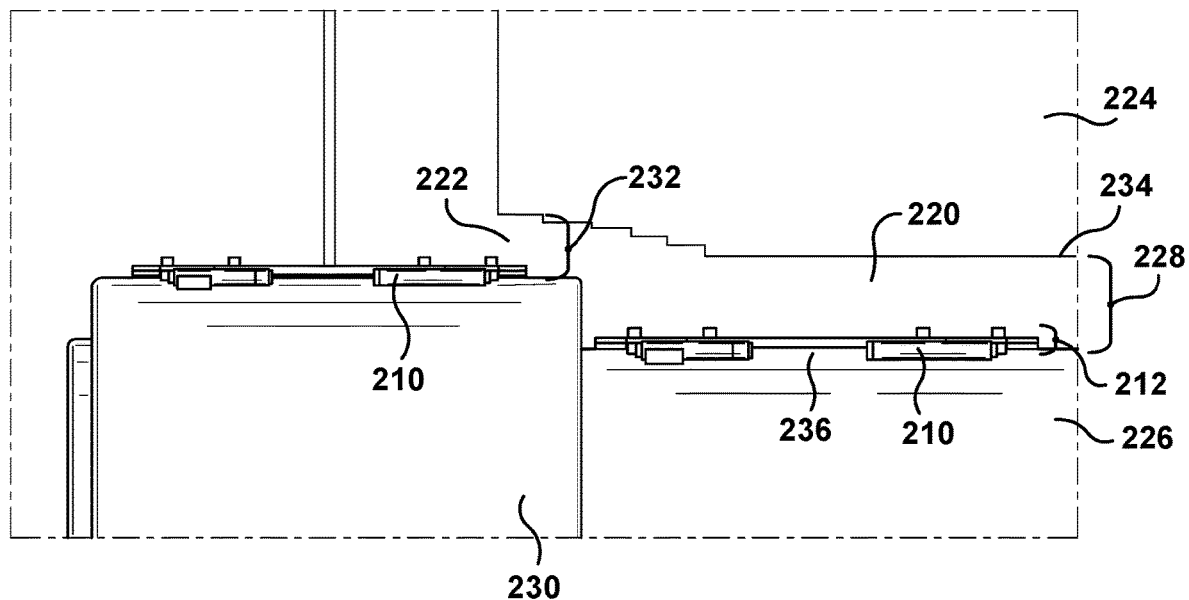
FIG. 2 shows a side cutaway view of gap insertion of a robotic crawler into a machine.

Referring to FIG. 2, an in situ gap inspection system 200 is shown with a robotic crawler 210, such as robotic crawler 110 in FIG. 1, being inserted into a machine 220. Machine 220 may be any machine with an annular gap 220 accessible through an entrance gap 222 and, more specifically, a variety of machine configurations of generators, electric motors, or turbomachines. For example, a generator may allow insertion through the air gap between the core iron and the retaining ring permits in situ inspection of the rotor and the stator core. Annular gap 220 may be defined between a cylindrical central member 226 and a surrounding cylindrical member 224 with generally complementary curvature. In some embodiments, annular gap 220 may be an air gap generally defined by: the inner diameter of the stator minus the outer diameter of the rotor divided by two. Annular gap 220 has an axial length from a first end to a second end of cylindrical central member 226 and a circumference measured in the direction of the circumference of cylindrical central member 226. Annular gap 220 has an annular gap width 228 measured from outer surface 236 of cylindrical central member 226 to the nearest opposite surface (inner surface 234) of surrounding cylindrical member 224. In some embodiments, entrance gap 222 may be an air gap at an end of the central cylindrical member 226 and have the same entrance width as annular gap width 228. In other embodiments, entrance gap 222 may include additional features, such as a retaining member 230, that further constrain entrance gap 222 and define an entrance gap width 232 is that is less than annular gap width 228. In some embodiments, additional features or obstacles may reduce annular gap width 228, such entrance baffles used to direct cooling air flow.

In FIG. 2, robotic crawler 210 is in a collapsed state, where its traction modules are aligned in a single plane. Robotic crawler 210 is shown outside entrance gap 222 before insertion and inside annular gap 220 after insertion. Robotic crawler 210 may define a collapsed crawler width 212. Collapsed crawler width 212 may be less than both entrance gap width 232 and annular gap width 228. In its collapsed state, robotic crawler 210 engages only outer surface 236 of central cylindrical member 226 inside annular gap 220.

Figure 3:
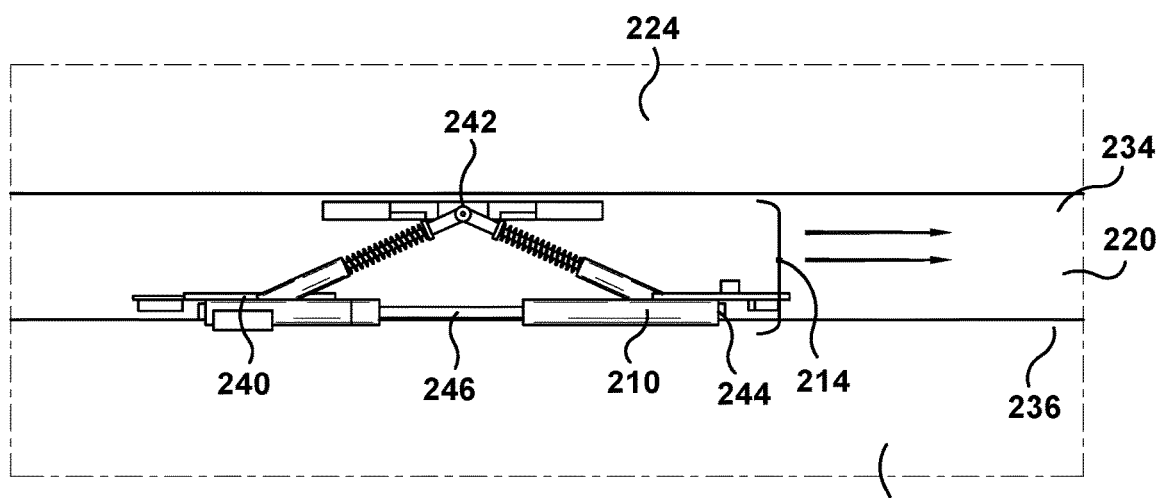
FIG. 3 shows a side cutaway view of an expanded robotic crawler in the annular gap of a machine.
Figure 4:
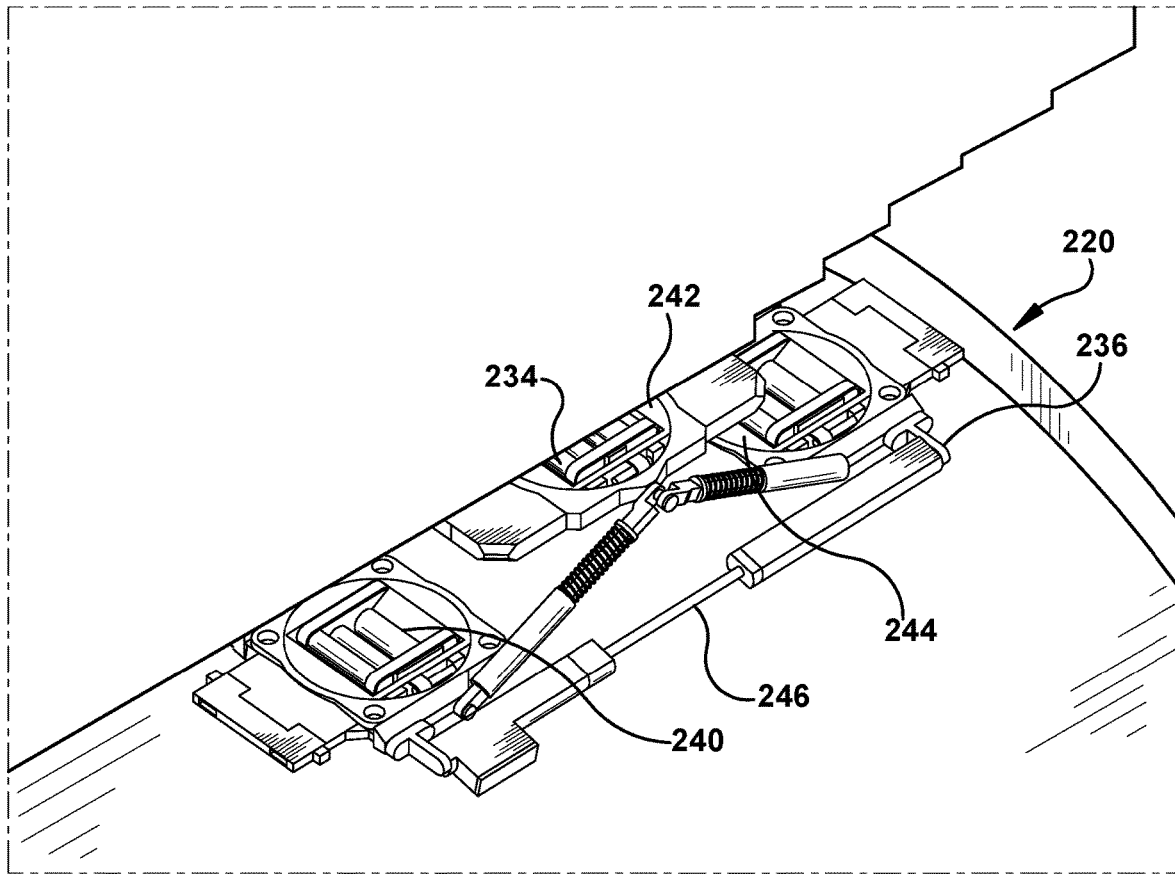
FIG. 4 shows a perspective cutaway view of an expanded robotic crawler in the annular gap of a machine.

FIGS. 3-4 show two views of robotic crawler 210 in an expanded state within annular gap 220. When robotic crawler 210 is in its expanded state, it may engage opposed surfaces 234, 236. In an expanded state, robotic crawler 210 may define an expanded crawler width 214. Expanded crawler width 214 may be larger than collapsed crawler width 212 and entrance gap width 232, and equal to annular gap width 228 such that surface contact may be maintained with opposed surfaces 234, 236. In some embodiments, robotic crawler 210 comprises a plurality of traction modules 240, 242, 244 mounted in an expandable body 246. Traction modules 240, 244 may engage only outer surface 236 of central cylindrical member 226 and traction module 242 may engage only inner surface 234 of surrounding cylindrical member 236. In some embodiments, the configuration of traction modules 240, 242, 244 may be reversed and traction modules 240, 244 may engage only inner surface 234 of surrounding cylindrical member 236 and traction module 242 may engage only outer surface 236 of central cylindrical member 226. Traction modules 240, 242, 244 may include rollers, including wheels, balls, or tracks, to move robotic crawler 210 through annular gap 220 based on moving surface contact with opposed surfaces 234, 236. Traction modules 240, 242, 244 may move robotic crawler 210 on a desired navigation path through annular gap 220.

Figure 5:
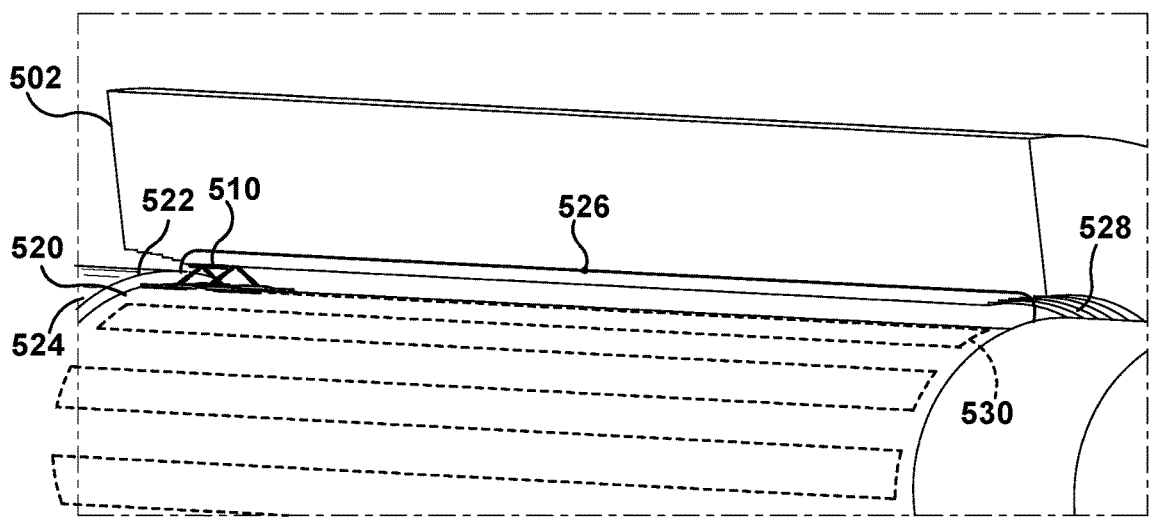
FIG. 5 shows an example inspection path of a robotic crawler in the annular gap of a machine.

Referring to FIG. 5, a robotic crawler 510 is shown in an annular gap 520 of a machine 500 with line 530 showing an example navigation path for inspecting annular gap 520 and deploying an end region visual inspection module (not shown). Robotic crawler 510 is shown in an expanded state in a starting crawler position just inside entrance gap 522 adjacent an entrance end portion 524 of the machine 502. Following line 530, robotic crawler 510 moves in a forward axial direction along a gap length 526 of annular gap 520 from entrance end portion 524 to closed end portion 528, such as the end winding region of a generator. For example, closed end portion 528 may be the drive end of machine 500 and access from entrance gap 522 at the collector end through annular gap 520 may prevent the need to disassemble the drive end for inspection. In some embodiments, robotic crawler 510 may reach a step or other obstacle representing the end of the navigable gap length 526 of annular gap 520. For example, closed end portion 528 may include a step created by a retaining ring or other feature and may include another air gap into an enclosed end region of the machine. As described herein, an end region visual inspection module may extend from robotic crawler 510 into closed end portion 528 for inspection. Robotic crawler 510 may include multidirectional traction modules that enable it to change its travel direction from the axial direction to the circumferential direction, as well as to reverse axial direction to return and exit annular gap 520 at entrance end portion 524. Robotic crawler 510 may follow a more complex navigation path to conduct other inspections or tests and may deploy the end region visual inspection module when it is proximate closed end portion 528.

Figure 6:
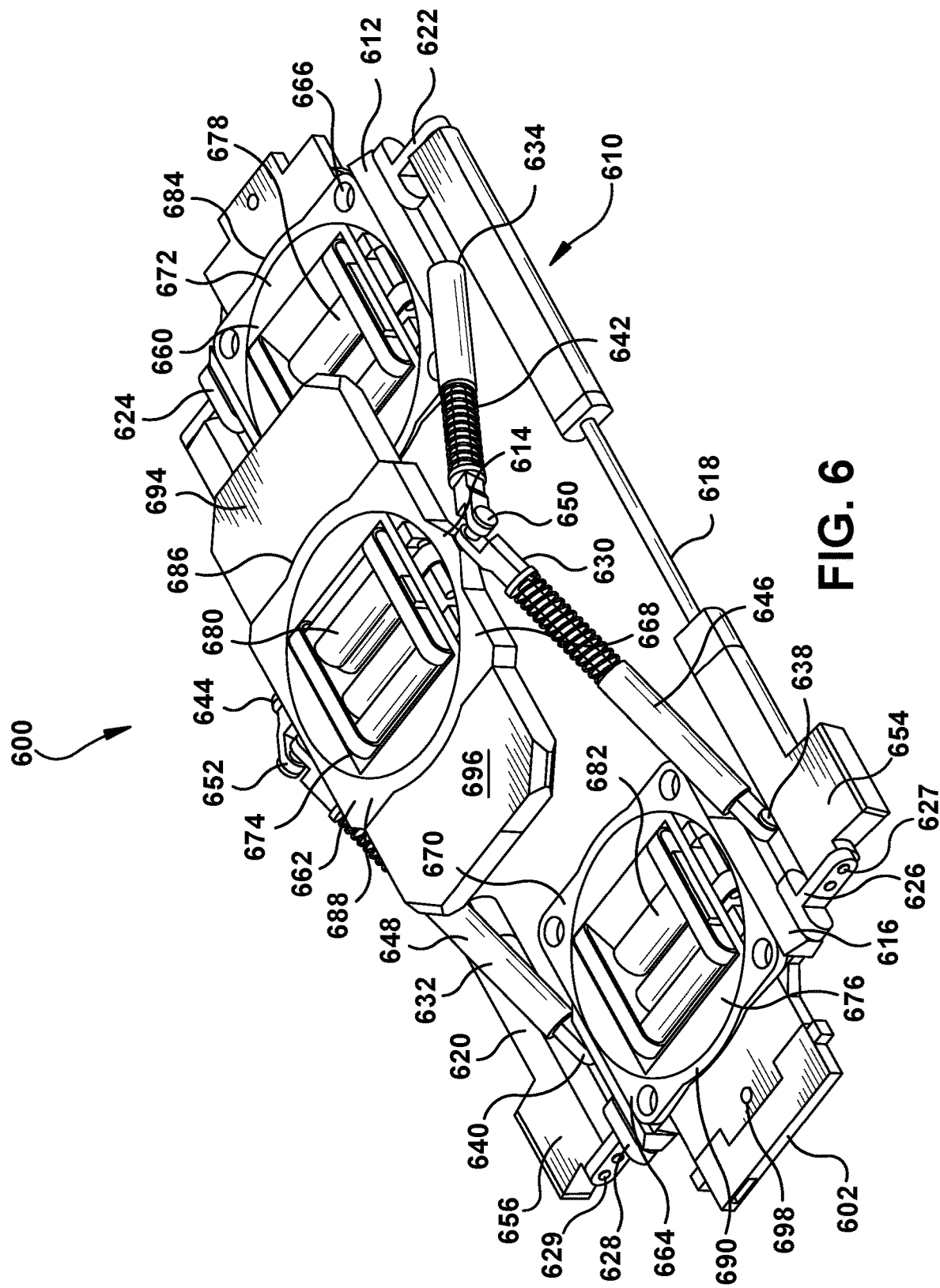
FIG. 6 shows a perspective view of a robotic crawler in its expanded state according to various embodiments of the disclosure.

Referring to FIGS. 6-8, an additional embodiment of a robotic crawler 600 is shown in several views and including an expanded state in FIG. 6 and a collapsed state in FIGS. 7-8. In some embodiments, robotic crawler 600 is a modular robot with an expandable body 610 including plurality of frames 612, 614, 616 for accommodating removable modules. Removable modules may include traction modules 660, 662, 664 that provide rollers, such as wheels, tracks, or balls, or another form of locomotion for moving robotic crawler 600 along the surfaces within a gap. Robotic crawler 600 may also accommodate a plurality of sensor modules, such as navigation sensors, visual inspection sensors, structural test sensors, or electrical test sensors, using sensor interfaces that provide mechanical and/or electrical/communication/control between robotic crawler 600 and the sensor modules. For example, one or more module frames may include sensor interfaces and/or the traction modules or other sensor modules may include sensor interfaces for chaining multiple modules from a single frame. The plurality of sensor interfaces may be provided at several positions on robotic crawler 600 to provide different operating positions for various sensors. For example, each of traction modules 660, 662, 664 may include one or more sensor interfaces and related sensor positions. In some embodiments, there may be multiple configurations of sensor interfaces. For example, sensor interfaces for attachment to traction modules 660, 662, 664 may be different than sensor interfaces between serial sensor interfaces. Other modules may also be provided for other functions, such as a tether connector module 602.

In some embodiments, expandable body 610 includes generally rectangular base frame and includes lateral members 618, 620 on the long sides of the rectangle, connected to front frame 612 and rear frame 616 providing the short sides of the rectangle. Lateral members 618, 620 may include frame attachments 622, 624, 626, 628 proximate their respective distal ends. Frame attachments 622, 624 may connect to front frame 612 and frame attachments 626, 628 may connect to rear frame 616. In some embodiments, middle frame 614 may be configured to be displaced from the plane of front frame 612 and rear frame 616 to expand the width of expandable body 610 in its expanded state.

Middle frame 614 may be attached to extension link members 630, 632, which are connected to the rectangular base frame. For example, extension link members 630, 632 may include pivoting attachments 634, 636, 638, 640 with front frame 612 and rear frame 616 or, alternately, with lateral members 618, 620 proximate their distal ends. Extension link members 630, 632 may be articulated link members with first links 642, 644 and second links 646, 648 having pivoting attachments 650, 652 to middle frame 614. Pivoting attachments 650, 652 may act as an articulated joint in extension link members 630, 632 and move middle frame 614 perpendicular to the plane of the rectangular base frame. Expandable body 610 may include a motor or other actuator for moving middle frame 614. For example, lateral members 618, 620 may include linear actuators 654, 656 for moving front frame 612 relative to rear frame 616, changing the lengths of lateral members 618, 620 and the distance between front frame 612 and rear frame 616. When lateral members 618, 620 are in their fully extended positions, front frame 612, middle frame 614, and rear frame 616 may be in the same plane and expandable body 610 is in its narrowest or collapsed state. As lateral members 618, 620 are shortened by linear actuators 654, 656 and rear frame 616 moves toward front frame 612, extension link members 630, 632 articulate at pivoting attachments 650, 652 and first links 642, 644, second links 646, 648, and lateral members 618, 620 form an isosceles triangle with middle frame 614 moving in a direction perpendicular to the direction of movement between front frame 612 and rear frame 616. Other configurations of expandable bodies are possible, such as one or more frames being mounted on lever arms, scissor jacks, telescoping members, or other displacement mechanisms. In some embodiments, expandable body 610 may incorporate shock absorbers between front frame 612 and rear frame 616 and middle frame 614 to assist in navigating uneven gap spaces. For example, extension link members 630, 632 may incorporate telescoping links with an internal spring to assist with traction on opposed gap surfaces and compensate for some obstacles and/or changes in gap spacing. In some embodiments, lateral members 618, 620 may include emergency releases 627, 629 to disengage lateral members 618, 620 manually in the event of power loss or other failure that prevents control of linear actuators 654, 656. For example, frame attachments 626, 628 may incorporate mechanical fasteners that attach lateral members 618, 620 to frame attachments 626, 628 and these mechanical fasteners may act as emergency releases 627, 629 by enabling a user to release the mechanical fasteners and thereby disengage lateral members 618, 620 to cause expandable body 610 to collapse into its collapsed state. In some embodiments, emergency releases 627, 629 may be screws, bolts, or pins through frame attachments 626, 628 and into lateral members 618, 620 that may be removed to collapse expandable body 610. In some embodiments, expandable body 610 has a lateral shape that is an arc based on the configuration of frames 612, 614, 616 and lateral members 618, 620, most visible in FIG. 8. The arc of expandable body 610 may be configured to complement the curvature of an annular gap in which robotic crawler 600 is intended to operate. For example, the arc or curvature may be similar to the arc of the outer surface of the central cylindrical member or the inner surface of the surrounding cylindrical member that define the annular gap.

In some embodiments, each of frames 612, 614, 616 are configured to receive, position, and retain traction modules 660, 662, 664. For example, traction modules 660, 662, 664 may each be multidirectional traction modules with fixed outer frames 666, 668, 670 to removably attach to frames 612, 614, 616. Traction modules 660, 662, 664 may include rotating inner frames 672, 674, 676 that enable robotic crawler 600 to change the orientation of rollers 678, 680, 682 and direction of movement. Each of traction modules 660, 662, 664 may also include one or more interfaces 684, 686, 688, 690 that may be used to attach sensor modules or other functional modules, directly or in series. For example, traction module 660 may include interface 684 and is shown with a visual sensor module 692. Traction module 662 may include interfaces 686, 688 and visual sensor modules 694, 696. Traction module 664 may include interface 670, visual sensor module 698, and tether connector module 602.

Figure 9:
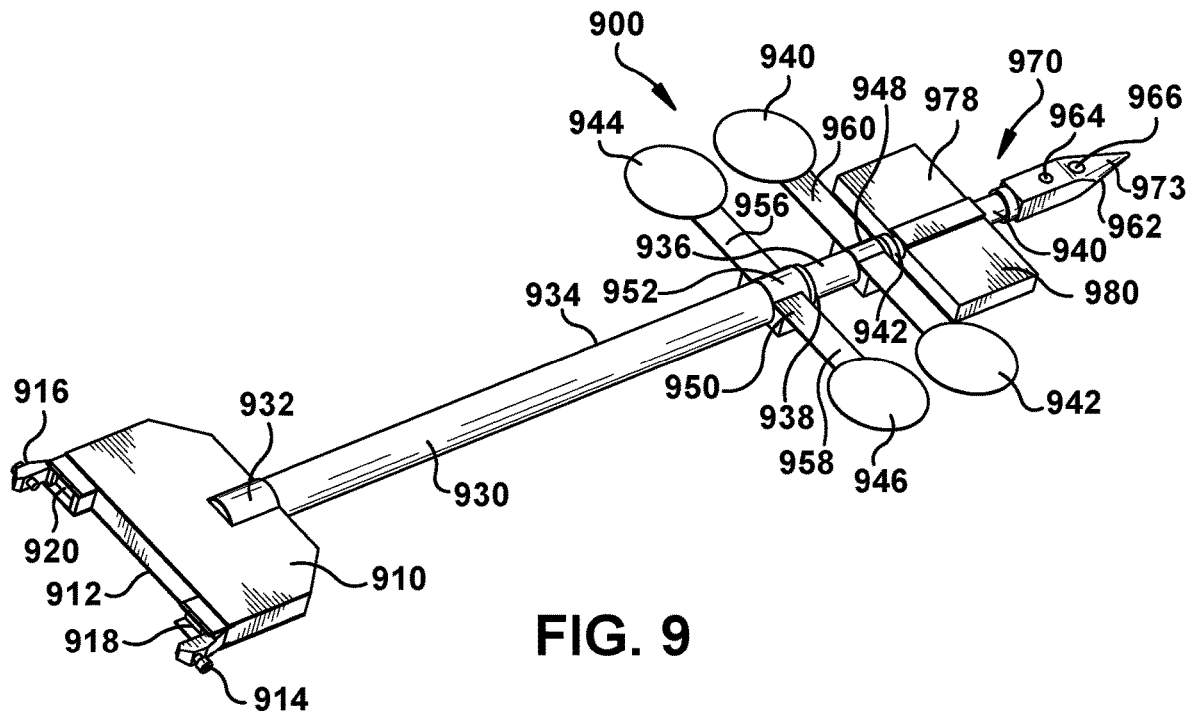
FIG. 9 shows a top perspective view of an example end region visual sensor module according to various embodiments of the disclosure.
Figure 10:
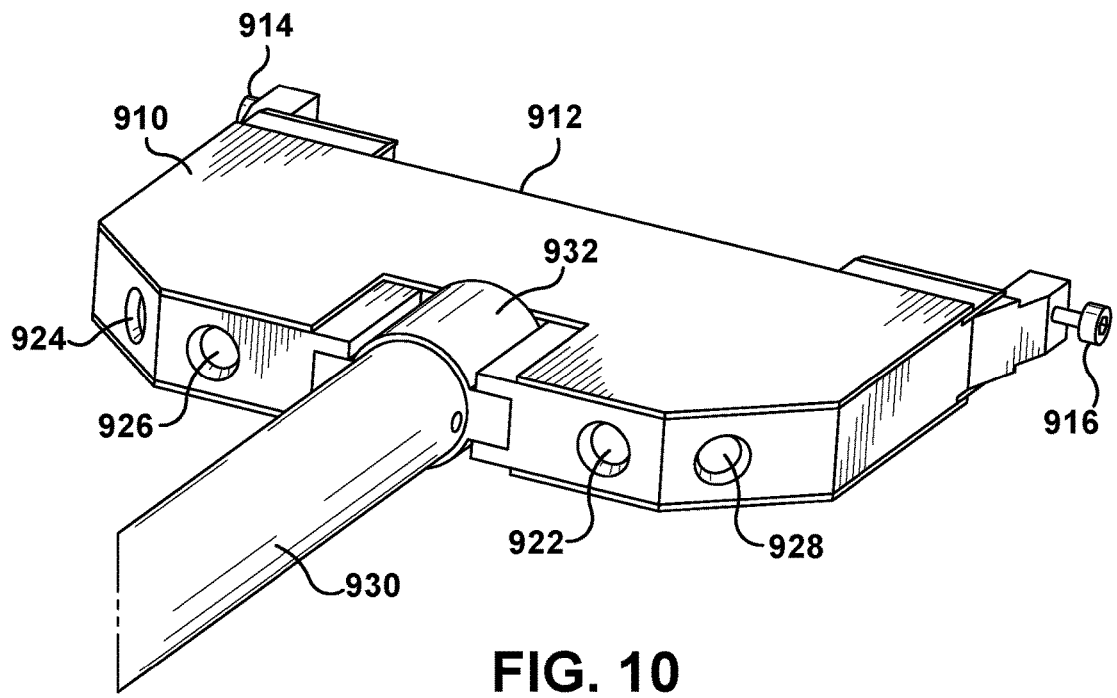
FIG. 10 shows a close-up top perspective of the connector assembly of the end region visual sensor module of FIG. 9.
Figure 11:
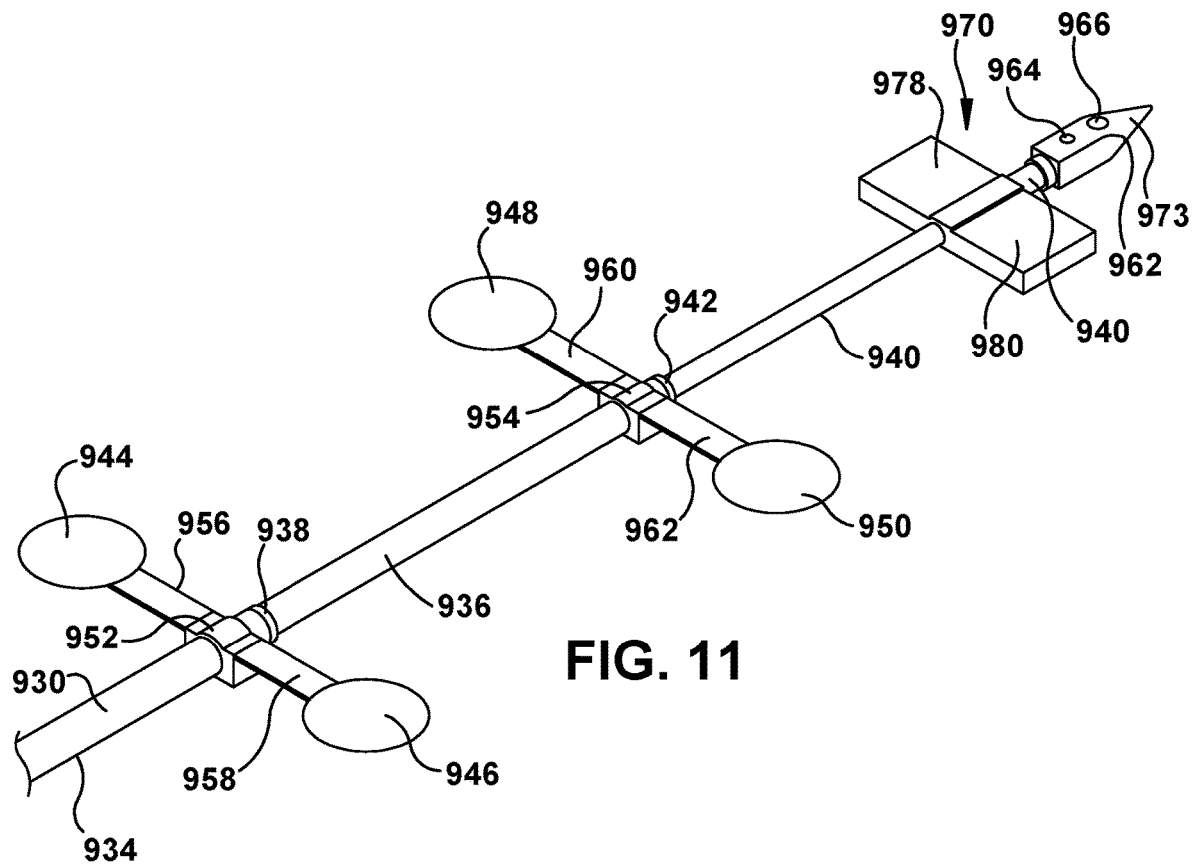
FIG. 11 shows a close up top perspective of the extension member of the end region visual sensor module of FIG. 9.

Referring to FIGS. 9-11, another configuration of a visual inspection sensor is shown as end region inspection module 900. End region inspection module 900 may be configured to extend into a region of a machine that a robotic crawler may not otherwise be able to reach and enable visual inspection of that region, such as an obstructed end region accessible through an inspection gap that is too narrow for the robotic crawler and/or inaccessible to the traction modules (or any other form of locomotion) of the robotic crawler.

End region inspection module 900 may include a module housing 910 defining a mounting interface 912 and accommodating fasteners 914, 916 for removably attaching end region inspection module 900 to a robotic crawler. For example, mounting interface 912 may be configured for removable attachment to a sensor interface on a robotic crawler, such as a sensor interface on a module mounting frame or a previously installed module, including a traction module with a sensor interface. In some embodiments, module housing 910 may include electronics, power source, communication channels, and/or test components to support and/or interface with other test components of end region inspection module 900. In some embodiments, mounting interface 912 may include a connectors 918, 920 for power and/or communication channels for control and/or data signals to and from end region inspection module 900. In some embodiments, end region inspection module 900 may include a fixed camera 922 and light sources 924, 926, 928 mounted on or in module housing 910.

End region inspection module 900 may include an extension member 930 connected to module housing 910. For example, extension member 930 may have a fixed mount 932 to module housing 910 and comprise a telescoping member with a fixed portion 934, a first telescoping portion 936, and a slidably positionable joint 938 between fixed portion 934 and first telescoping portion 936. In some embodiments, extension member 930 may include a second telescoping portion 940 and a slidably positionable joint 942 between first telescoping portion 936 and second telescoping portion 940. FIG. 11 shows extension member 930 in an extended configuration with both first telescoping portion 936 and second telescoping portion 940 extended. In some embodiments, slidably positionable joints 938, 942 may include torque clamps, such as manual torque clamps that allow the length of extension member 930 to be adjusted prior to deployment into the annular gap of a machine. In some embodiments, extension member 930 may include length increments marked on the surface of extension member 930 to facilitate adjustment to a desired length. In some embodiments, extension member 930 may include an actuator (not shown) extending through first telescoping portion 936 and second telescoping portion 940 and in communication with the robotic crawler or the control unit to adjust the length of extension member 930 during operation of the robotic crawler within the gap. In some embodiments, slidably positionable joints 938, 942 may also include positionable rotation of first telescoping portion 936 and second telescoping portion 940. Extension member 930 may also include one or more channels (not shown) for connecting power, control, or data channels from module housing 910 to a sensor head assembly 970. For example, extension member 930 may include an interior space, such as interior tubing or a chase, running the length of extension member 930 and carrying one or more wires or similar connections from module housing 910 to sensor head assembly 970. In some embodiments, extension member 930 may include a plurality of member sections (not shown) of predetermined lengths that may be assembled, added to, or removed from extension member 930 to adjust the length of extension member 930. In some embodiments, these additive member sections may be used in combination with one or more telescoping members and in others they may be used in lieu of a telescoping configuration.

Extension member 930 may include one or more slidable supports that assist with positioning extension member 930. For example, extension member 930 may include slidable magnetic pads 944, 946, 948, 950 in laterally spaced pairs supported by brackets 952, 954 and flexible members 956, 958, 960, 962. Slidable magnetic pads 944, 946, 948, 950 may combine a magnetic core configured to provide an attachment force to one or more magnetic surfaces of the machine with a non-stick pad surface configured to move along the magnetic surface. Slidable magnetic pads 944, 946, 948, 950 may be slidable on and detachable from the surface of the machine under the motive force of the robotic crawler, the telescoping member, or another positioning element. Slidable magnetic pads 944, 946, 948, 950 may be spaced laterally from extension member 930 by flexible members 956, 958, 960, 962. Flexible members 956, 958, 960, 962 may hold slidable magnetic pads 944, 946, 948, 950 in a generally planar configuration while allowing them to flex toward and match the curvature of the surfaces in the annular gap to which they adhere. For example, flexible members 956, 958, 960, 962 may be rigid enough to support slidable magnetic pads 944, 946, 948, 950 laterally from extension member 930 while providing 1-5 inches of flexion to curve toward the adjacent surface under the magnetic force of slidable magnetic pads 944, 946, 948, 950. In one embodiment, one pair of slidable magnetic pads 944, 946 may be attached to fixed portion 932 by bracket 952 and the other pair of slidable magnetic pads 948, 950 may be attached to first telescoping portion 936 by bracket 954. Note that while the example is shown with a configuration of four pads, other configurations with any number of pads may also be feasible. Engagement of slidable magnetic pads 944, 946, 948, 950 may limit deflection of extension member 930 and minimize oscillation during deployment and use of sensors on extension member 930. In some embodiments, flexible members 956, 958, 960, 962 may be replaced with rigid members with a fixed geometry matched to the curvature of the surface on which slidable magnetic pads 944, 946, 948, 950 are intended to slidably engage.

Extension member 930 may connect to and support a sensor head assembly 970 at the distal end of extension member 930. The example end region inspection module 900 is described in terms of a visual inspection sensor module incorporating a camera, but other inspection or testing modules could be used with extension member 930 for other inspections or tests in difficult to reach regions of a machine. In some embodiments, sensor head assembly 970 may include a sensor housing 972 with a camera 974, such as a digital video camera, and a light source 976, such as an LED with diffuser. In some embodiments, sensor housing 972 may include a tapered end 973 to assist in guiding sensor head assembly 970 through obstacles. Sensor head assembly 970 may further include an electronics module 978 and a motor module 980. For example, electronics module 978 may include electronics for processing visual data collected by camera 974 and communicating that visual data to the robotic crawler or control unit, such as by wired or wireless video streaming, and motor module 980 may provide a motor, position index, and control interface for controllably moving rotating housing 972, camera 974, and light source 976 during an inspection protocol. For example, a rotating camera configuration may enable panning around the axis of extension member 930 during an inspection protocol.

Figure 12:
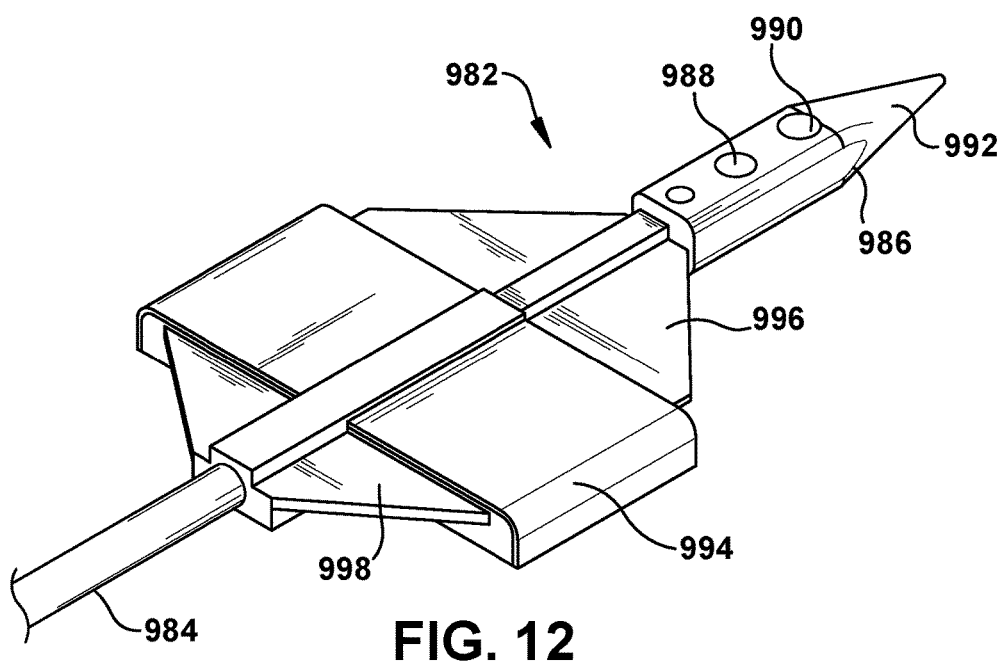
FIG. 12 shows a close-up top perspective of an example sensor head assembly for use with an end region visual sensor module according to various embodiments of the disclosure.

Referring to FIG. 12, another example configuration of a sensor head assembly 982 is shown operatively attached to an extension member 984, similar to extension member 930 (FIGS. 9-11). Sensor head assembly 982 may include a sensor housing 986 with a camera 988, such as a digital video camera, and a light source 990, such as an LED with diffuser. In some embodiments, sensor housing 986 may include a fixed camera orientation and sensor housing 986. Sensor housing 986 may include a tapered end 992 to assist in guiding sensor head assembly 982 through obstacles. Sensor head assembly 982 may further include an electronics module 994. For example, electronics module 994 may include electronics for processing visual data collected by camera 988 and communicating that visual data to the robotic crawler or control unit, such as by wired or wireless video streaming. Sensor head assembly 982 may include a forward shield 996 and a reverse shield 998. For example, forward shield 996 and reverse shield 998 may each be tapered toward the width of electronics module 994 to deflect obstacles and assist in guiding head assembly through obstacles in both forward and reverse directions of travel.

Figure 13:
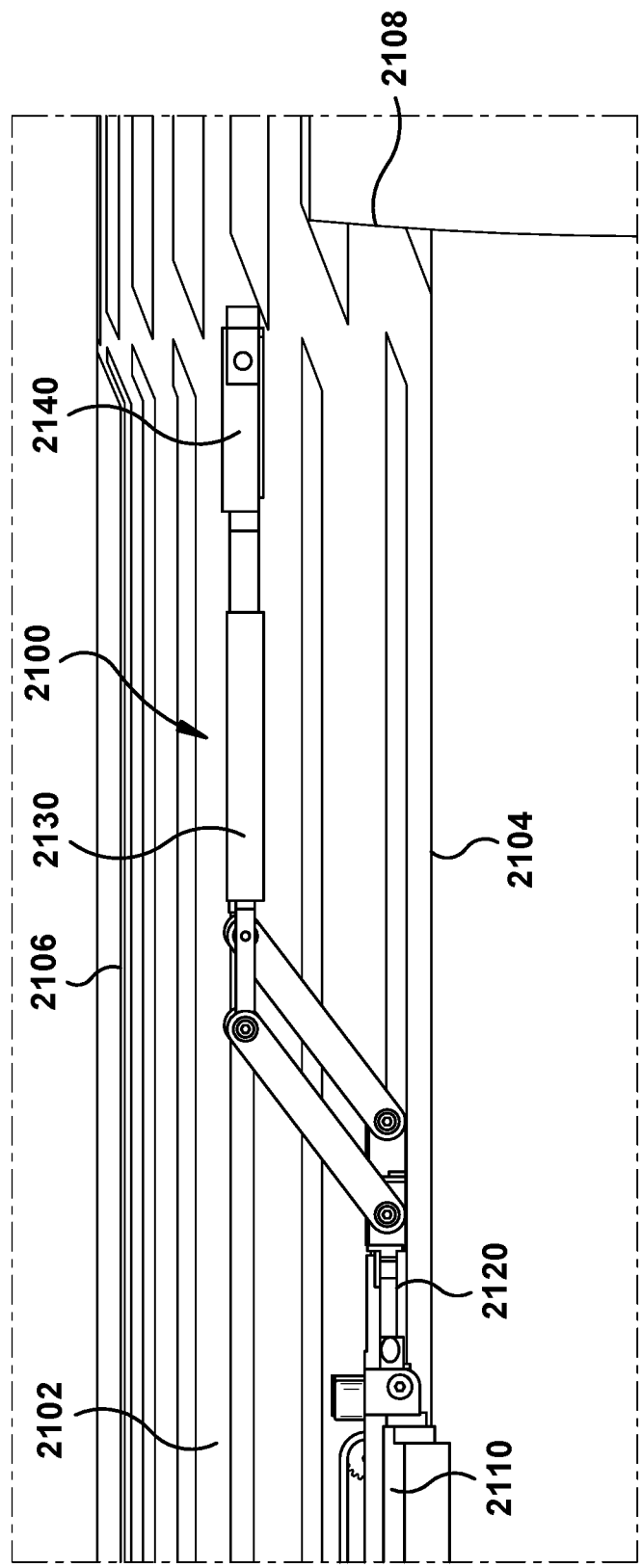
FIG. 13 shows a side cutaway view of an example deployment of an end region visual sensor module in the annular gap of a machine.

Referring to FIG. 13, a mechanical positioning module 2100 is shown according to various embodiments. Mechanical positioning module 2100 may be used to position a sensor module within the gap and relative to a crawler position of a robotic crawler. For example, mechanical positioning module may include one or more positionable joints to move a sensor interface (and an attached sensor module) to a desired height between the machine surfaces that define the gap. Mechanical positioning module 2100 is shown in a gap 2102 between a first surface 2104 and a second surface 2106 and attached to a robotic crawler 2110 positioning a sensor interface housing 2140 to clear a lip 2108. In some embodiments, mechanical positioning module 2100 includes a mounting interface housing 2120 that connects to a sensor interface of robotic crawler 2110, a mechanical positioning assembly 2130 connected to mounting interface housing 2120 at one end, and sensor interface housing 2140 connected to the other end of mechanical positioning assembly 2130. For example, mounting interface housing 2120 may include a mounting interface similar to those described above for sensor modules and compatible with one or more sensor interfaces on robotic crawler 2110. Mounting interface housing 2120 may include a motor and other components for receiving control signals and controlling the position of mechanical positioning assembly 2130. Mechanical positioning assembly 2130 may include a variety of positionable joints, members, and actuators for performing the desired positioning operations, such as a parallel lift capable of raising and lowering sensor interface housing 2140 while maintaining it on plane parallel to the base of robotic crawler 2110. Sensor interface housing 2140 may provide a sensor interface similar to those described above for receiving, positioning, and connecting a sensor module. In some embodiments, sensor interface housing 2140 may be replaced with a sensor housing for an integrated sensor module with a positioning assembly.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A system comprising:
   a robotic crawler configured to navigate within an annular gap of a machine using a plurality of traction modules;
   a visual inspection module connected to the robotic crawler and including:
      an extension member,
      at least one camera at a distal end of the extension member, the at least one camera positioned laterally beyond the plurality of traction modules, and
      at least one magnetic sliding pad connected to the extension member and configured to engage a surface of the machine and position the extension member; and
   a visual display in communication with the robotic crawler and configured to display visual inspection data from the at least one camera.

2. The system of claim 1, wherein the machine includes an end region inaccessible to the plurality of traction modules, and the extension member is configured to extend into the end region from a crawler position in the annular gap.

3. The system of claim 1, wherein the robotic crawler includes a sensor interface and the visual inspection module has a fixed connection to the robotic crawler at the sensor interface, and wherein the visual inspection module further comprises at least one positionable joint that aligns the extension member relative to the robotic crawler.

4. The system of claim 3, wherein the plurality of traction modules includes a plurality of multidirectional traction modules configured to position the robotic crawler in an axial direction and a radial direction within the annular gap and the at least one positionable joint is a parallel lift that positions the extension member at a desired height between the opposed surfaces.

5. The system of claim 1, wherein the extension member includes a telescoping portion configured to adjust an extension length from the robotic crawler to a visual inspection location.

6. The system of claim 1, wherein the machine includes an end region inaccessible to the plurality of multidirectional traction modules and the extension member is configured to extend into the end region from a crawler position in the annular gap, and wherein the at least one magnetic sliding pad includes a plurality of magnetic sliding pads extending laterally from the extension member to engage the surface within the end region.

7. The system of claim 1, wherein the at least one magnetic sliding pad is supported by a flexible member extending laterally from the extension member.

8. The system of claim 1, wherein the visual inspection module further includes a motorized position controller in communication with the visual display that controllably rotates the at least one camera to a desired position.

9. The system of claim 1, wherein the visual inspection module further includes at least one light source.

10. The system of claim 1, wherein the machine is selected from a generator, an electric motor, or a turbomachine, and includes an entrance gap accessible when a first end of the machine is removed from the machine and an end region at a second end of the machine opposite the first end, wherein the robotic crawler is configured to be inserted through the entrance gap into the annular gap and navigate the annular gap to a crawler position adjacent the second end, and wherein the extension member is configured to extend into the end region from the crawler position in the annular gap to inspect the end region using the at least one camera.

11. A method comprising:
   removing a first end portion at a first end of a machine to expose an entrance gap into an annular gap of the machine, the machine selected from a generator, an electric motor, or a turbomachine;
   inserting a robotic crawler through the entrance gap into the annular gap of the machine;
   traversing the annular gap with the robotic crawler to a crawler position adjacent a second end portion of the machine at a second end opposite the first end; and
   performing a visual inspection of the second end portion of the machine using a visual inspection module connected to the robotic crawler and including an extension member and at least one camera.

12. The method of claim 11, wherein the second end region is a drive end of a machine inaccessible to a plurality of traction modules of the robotic crawler and the extension member is configured to extend into the second end region from the crawler position in the annular gap, and the traversing includes driving the plurality of traction modules in an axial direction through the annular gap until the visual inspection module is within the drive end of the machine.

13. The method of claim 11, wherein the visual inspection module further comprises at least one positionable joint for aligning the extension member relative to the robotic crawler, the method further comprising positioning the at least one camera to inspect the second end region using the at least one positionable joint.

14. The method of claim 11, wherein the extension member includes a telescoping portion, the method further comprising adjusting an extension length from of the extension member from the robotic crawler to a visual inspection location.

15. The method of claim 11, wherein the visual inspection module further includes at least one magnetic sliding pad, the method further comprising positioning the at least one camera by engaging a second end region surface of the machine with the at least one magnetic sliding pad and sliding the at least one magnetic sliding pad along the second end region surface.

16. The method of claim 11, wherein the visual inspection module further includes a motorized position controller and performing the visual inspection includes controllably rotating the at least one camera to a plurality of desired positions.

17. A visual inspection module for a robotic crawler comprising:
 a crawler interface configured for removable attachment to the robotic crawler;
 an extension member extending from the crawler interface and configured to extend from the robotic crawler positioned in an annular gap of a machine into an end portion of the machine inaccessible to the robotic crawler;
 at least one camera disposed at a distal end of the extension member and positionable to collect visual data from the end portion of the machine;
 at least one magnetic sliding pad connected to the extension member and configured to engage a surface of the machine and position the extension member; and
 at least one communication channel configured to receive control signals from the visual inspection module and provide visual data to a visual display.

18. The visual inspection module of claim 17, further comprising an electronics module proximate the distal end of the extension member for processing collected visual data and transmitting visual data through the at least one communication channel.

* * * * *